(12) United States Patent
Chan et al.

(10) Patent No.: US 9,655,559 B2
(45) Date of Patent: May 23, 2017

(54) AUTOMATED SLEEP STAGING USING WEARABLE SENSORS

(71) Applicant: Vital Connect, Inc., Campbell, CA (US)

(72) Inventors: Alexander Chan, Campbell, CA (US); Ravi Narasimhan, Sunnyvale, CA (US)

(73) Assignee: Vital Connect, Inc., San Jose, CA (US)

(*) Notice: Subject to any disclaimer, the term of this patent is extended or adjusted under 35 U.S.C. 154(b) by 478 days.

(21) Appl. No.: 14/147,413

(22) Filed: Jan. 3, 2014

(65) Prior Publication Data

US 2015/0190086 A1 Jul. 9, 2015

(51) Int. Cl.
*A61B 5/00* (2006.01)

(52) U.S. Cl.
CPC .................. *A61B 5/4812* (2013.01)

(58) Field of Classification Search
CPC .................................................. A61B 5/4812
See application file for complete search history.

(56) References Cited

U.S. PATENT DOCUMENTS

| | | | |
|---|---|---|---|
| 7,502,643 B2 | 3/2009 | Farringdon et al. | |
| 2006/0009704 A1 | 1/2006 | Okada et al. | |
| 2007/0015976 A1 | 1/2007 | Miesel et al. | |
| 2007/0249952 A1* | 10/2007 | Rubin | A61B 5/0476 600/544 |
| 2009/0131803 A1 | 5/2009 | Heneghan et al. | |
| 2011/0218454 A1 | 9/2011 | Low | |
| 2011/0295142 A1* | 12/2011 | Chakravarthy | A61B 5/0476 600/544 |
| 2012/0238800 A1* | 9/2012 | Naujokat | A61B 5/0402 600/26 |

OTHER PUBLICATIONS

The International Search Report and the Written Opinion of the International Searching Authority issued on Apr. 10, 2015 for International Application No. PCT/US2015/010190.

* cited by examiner

*Primary Examiner* — Eric D. Bertram
(74) *Attorney, Agent, or Firm* — Brundidge & Stanger, P.C.

(57) ABSTRACT

A method and system for automated sleep staging are disclosed. The method comprises determining at least one physiological signal during a predetermined time period, extracting at least one feature from the at least one physiological signal, and classifying the at least one feature using a machine learning classifier to output at least one sleep stage. The system includes a sensor to determine at least one physiological signal during a predetermined time period, a processor coupled to the sensor, and a memory device coupled to the processor, wherein the memory device includes an application that, when executed by the processor, causes the processor to extract at least one feature from the at least one physiological signal and to classify the at least one feature using a machine learning classifier unit to output at least one sleep stage.

9 Claims, 4 Drawing Sheets

AUTOMATED SLEEP STAGING USING WEARABLE SENSORS

FIELD OF THE INVENTION

The present invention relates to wireless sensor devices, and more particularly, to automated sleep staging using the wireless sensor devices.

BACKGROUND

Sleep staging is important for understanding the quality of sleep and for the diagnosis of various sleep disorders (e.g. insomnia, parasomnias, REM behavior disorder, etc.). There are 5 stages of sleep (according to the new AASM guidelines) which include Stage W (wake), Stage N1 (lightest non-REM sleep), Stage N2 (mid-level stage of non-REM sleep), Stage N3 (deep non-REM sleep), and Stage REM (rapid eye movement sleep where dreaming occurs).

Conventionally, sleep staging of a person is done via a full clinical polysomnography (PSG) study where a technician splits the night into 30 second epochs or time periods and then assigns one of the 5 stages of sleep to each epoch. At a minimum, a PSG study requires signals that are relatively obtrusive and uncomfortable, including electroencephalography (EEG), electromyography (EMG), and electrooculography (EOG). The abundance of sensors required to detect the EEG, EMG, and EOG signals interferes with the person's sleep and prevents a representative sample of sleep from being obtained. Additionally, the PSG study is typically done outside of the home and in a sleep lab, making the environment different than the person is used to. Also, staging of the PSG study requires a trained technician to manually review the PSG study which can often take several hours and is highly subjective.

Therefore, there is a strong need for a cost-effective, and efficient solution that overcomes the aforementioned issues. The present invention addresses such a need.

SUMMARY OF THE INVENTION

A method and system for automated sleep staging are disclosed. The method comprises determining at least one physiological signal during a predetermined time period, extracting at least one feature from the at least one physiological signal, and classifying the at least one feature using a machine learning classifier to output at least one sleep stage.

The system includes a sensor to determine at least one physiological signal during a predetermined time period, a processor coupled to the sensor, and a memory device coupled to the processor, wherein the memory device includes an application that, when executed by the processor, causes the processor to extract at least one feature from the at least one physiological signal and to classify the at least one feature using a machine learning classifier unit to output at least one sleep stage.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

The present invention relates to wireless sensor devices, and more particularly, to automated sleep staging using the wireless sensor devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

The stages of sleep are typically defined by brain signals derived from an electroencephalography (EEG) study. However, cardiorespiratory and other physiological measures also change across the different stages of sleep: heart rate variability (HRV) can increase with deeper sleep; respiratory variability can increase with deeper sleep; skin temperature can increase at sleep onset; and little to no movement is observed during REM sleep because the body is paralyzed.

In one embodiment, a wireless sensor device with an embedded sensor and electrodes is attached to a user to detect less obtrusive raw physiological signals including an electrocardiogram (ECG) signals (e.g. a single-lead, bipolar ECG signal), accelerometry signals, and skin temperature signals. The physiological signals are detected by the wireless sensor device over a plurality of predetermined time periods or windows (e.g. every 4 minutes). The wireless sensor device combines and processes the detected physiological signals utilizing an automatic sleep staging process to record and to analyze more natural sleep conditions while the user sleeps at home.

The automatic sleep staging process extracts and calculates a plurality of features from the detected physiological signals, utilizes a machine learning classifier to classify each of the plurality of predetermined time windows into the 5 stages of sleep (W, N1, N2, N3, or REM), and feeds the outputs of the machine learning classifier into an algorithm that takes into account temporal dynamics of sleep and smoothens the outputted stages of sleep.

A method and system in accordance with the present invention automatically and continuously stages sleep of a user based on features derived from physiological signals including but not limited to ECG signals, triaxial accelerometer signals, skin temperature signals, breathing and respiratory signals, and EEG signals that are detected and processed by a wireless sensor device (also known as a wearable sensor) that can be attached to the user in any orientation.

In another embodiment, after the wireless sensor device detects various physiological signals, the wireless sensor device transmits the physiological signals to a remote server running in a cloud computer system. The remote server processes the physiological signals utilizing a machine learning classifier unit and an algorithm unit in a similar fashion as the processor of the wireless sensor device to calculate the plurality of features and account for temporal dynamics utilizing an application and algorithm running on the remote server.

Figure 1:
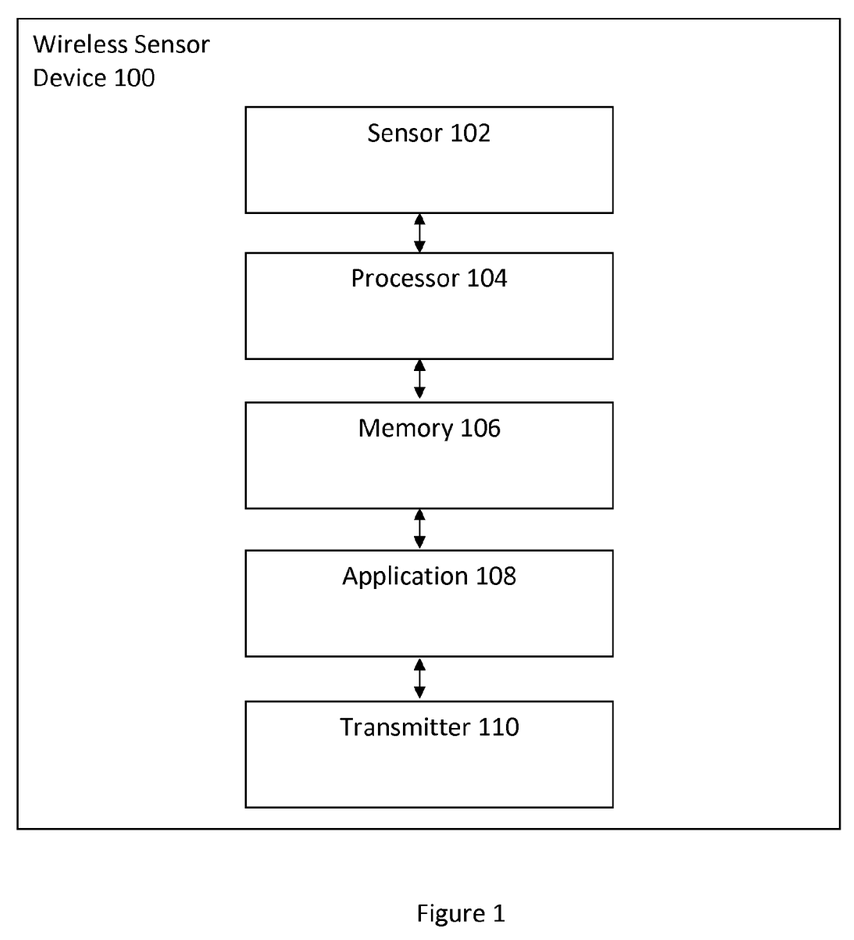
FIG. 1 illustrates a wireless sensor device for automated sleep staging in accordance with an embodiment.

FIG. 1 illustrates a wireless sensor device 100 for automated sleep staging in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. In one embodiment, the wireless sensor device 100 is attached to a user to detect various physiological signals via the sensor 102. The sensor 102 obtains data from the user which is transmitted to the memory 106 and in turn to the application 108 via the processor 104. The processor 104 executes the application 108 to obtain information regarding the user's health. The information is transmitted to the transmitter 110 and in turn relayed to another user or device. In another embodiment, the transmitter 110 transmits the various detected physiological signals in raw form to a remote server for processing and analysis.

In one embodiment, the sensor 102 is any of a microelectromechanical system (MEMS) tri-axial accelerometer and an embedded sensor with electrodes and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention. Additionally, one of ordinary skill in the art readily recognizes that a variety of wireless sensor devices can be utilized including but not limited to wearable sensors, a wireless sensor device in a patch form-factor, tri-axial accelerometers, uni-axial accelerometers, bi-axial accelerometers, gyroscopes, and pressure sensors and that would be within the spirit and scope of the present invention.

To describe the features of the present invention in more detail, refer now to the following description in conjunction with the accompanying Figures.

Figure 2:
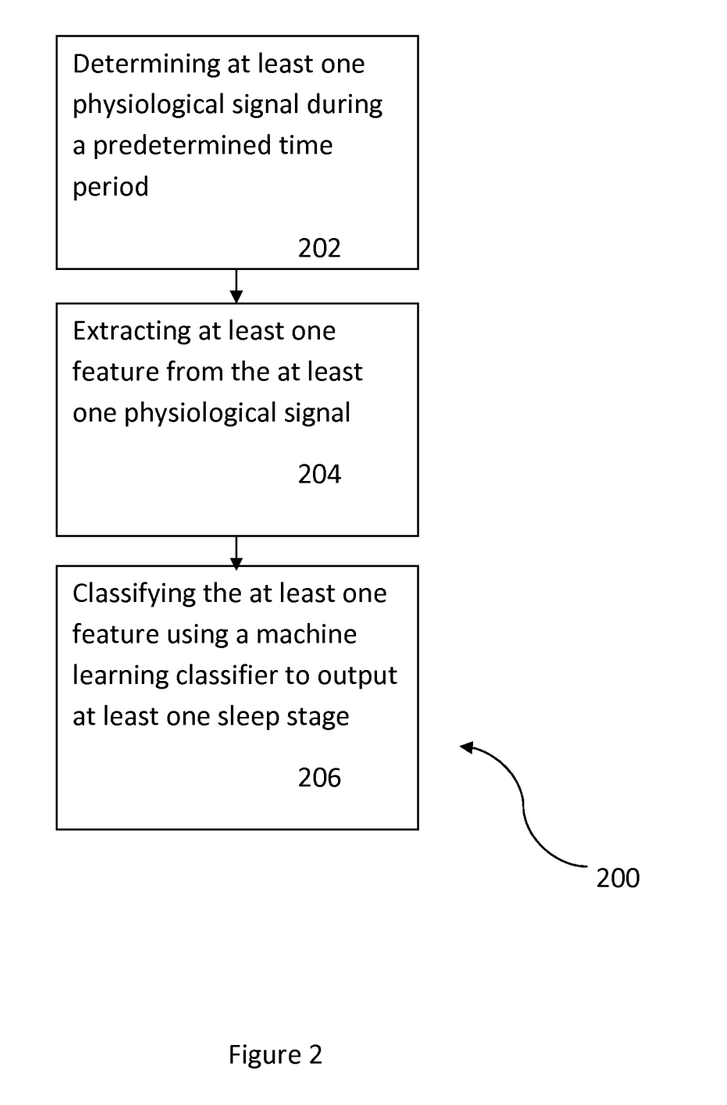
FIG. 2 illustrates a method for automated sleep staging by a wireless sensor device in accordance with an embodiment.

FIG. 2 illustrates a method 200 for automated sleep staging by a wireless sensor device in accordance with an embodiment. The method 200 includes determining at least one physiological signal during a predetermined time period via step 202, extracting at least one feature from the at least one physiological signal via step 204, and classifying the at least one feature using a machine learning classifier to output at least one sleep stage via step 206.

In one embodiment, the method 200 further comprises adjusting the at least one outputted sleep stage based on temporal dynamics. In another embodiment, the method 200 further comprises scaling the at least one feature to enable the machine learning classifier to deal with features of varying magnitudes and training the machine learning classifier using a data set of sleep stages derived from a polysomnography (PSG) study.

The wireless sensor device is attached to a user and is capable of detecting and determining a plurality of physiological signals of the user including but not limited to an electrocardiogram (ECG) signal, a microelectromechanical system (MEMS) accelerometer signal, a skin temperature signal, and an electroencephalography (EEG) signal. In one embodiment, the wireless sensor device continuously and automatically determines the plurality of physiological signals over a plurality of predetermined time periods that occur over another predetermined time period including but not limited to an eight hour period while the user is at home and sleeping. Each of the plurality of predetermined time periods include but are not limited to four minute time periods.

The machine learning classifier utilized by the wireless sensor device includes but is not limited to a support vector machine (SVM) classifier, a Naïve Bayes classifier (NBC), and an artificial neural network (ANN) classifier. In one embodiment, the machine learning classifier is a support vector machine (SVM) classifier that outputs a plurality of class probabilities for the five sleep stages (W, N1, N2, N3, REM). The plurality of class probabilities are then inputted into an algorithm that adjusts the plurality of outputted class probabilities based on temporal dynamics. The algorithm includes but is not limited to a Hidden Markov Model (HMM) algorithmic process that considers temporal dynamics of sleep stage transitions to smooth and increase the accuracy of the plurality of outputted class probabilities.

In one embodiment, the wireless sensor device extracts a plurality of features from the plurality of detected physiological signals by generating a feature vector for each predetermined time period of the plurality of predetermined time periods. In this embodiment, the plurality of features that are extracted include but are not limited to cardiovascular features, time-domain respiratory features, time-frequency respiratory features, cross-spectral respiratory features, and other features.

In another embodiment, the wireless sensor device extracts a plurality of features from the plurality of detected physiological signals by dividing each of the plurality of detected physiological signals into overlapping time period windows that are shifted every few seconds (e.g. every 30 seconds) so that the window centers of each of the plurality of detected physiological signals are aligned. The shifting of overlapping time period windows results in a plurality of epochs that are analyzed by the wireless sensor device or by a remote server that includes at least one algorithmic processing unit and associated algorithms. Typical time period windows include but are not limited to 4 minutes for respiratory signals, 2 minutes for heart rate variability signals, 1 minute for activity/accelerometer signals, and 1 minute for temperature signals.

For each epoch of the plurality of epochs, a plurality of features (e.g. mean, standard deviation, frequency-domain features, entropy, etc.) are calculated that characterize different relevant aspects of the plurality of detected physiological signals. A feature vector is generated for each epoch of the plurality of epochs and the feature vector consists of the plurality of features. The feature vector is inputted into the machine learning classifier that is utilized by the wireless sensor device to automatically classify each epoch into one of the 5 stages of sleep.

In one embodiment, the plurality of features are extracted from the following signals: an ECG signal is detected to derive R-R intervals that are resampled at 4 Hz (time between subsequent R-peaks), a triaxial accelerometer signal is detected, a respiratory signal is derived from the combination of the ECG signal and the triaxial accelerometer signals, and a skin temperature is detected. If an EEG signal is also detected by the wireless sensor device in another embodiment, the generated feature vector would consist of a greater number of features.

The plurality of features related to the cardiovascular features include but are not limited to the standard deviation of normal R-R intervals in a predetermined time period (SDNN), root-mean-square of sequential differences of normal R-R intervals (RMSSD), proportion of sequential differences of R-R intervals that are less than 50 milliseconds (pNN50), power of the R-R interval signal between 0.01-0.04 Hz or very low frequency (VLF), power of the R-R interval signal between 0.04-0.1 Hz or low frequency (LF), power of the R-R interval signal between 0.1-0.4 Hz or high frequency (HF), ratio of LF to HF (LF/HF), total power of the R-R interval signal (TP), maximum power in the VLF/LF/HF ranges respectively (VLF max, LF max, HF max), frequency corresponding to the maximum power in the VLF/LF/HF ranges respectively (Freq. of VLF max, Freq. of LF max, Freq. of HF max), mean absolute deviation of the R-R interval series (MAD), interquartile range of the R-R interval series (IQR), mean of the R-R intervals (RR mean), median of the R-R intervals (RR median), ratio of SDNN to RR mean (SDNN/(RR mean)), mean heart rate in a predetermined time period (HR), mean absolute deviation of the sequential differences of R-R intervals (MADSD), and SDNN of the R-R interval signal that has been lowpass filtered at 0.01 Hz (SDNN of filtered HRV).

The plurality of features related to the time-domain respiratory features include but are not limited to the mean breathing rate (BR mean), standard deviation of instantaneous breathing rate in a predetermined time period (BR std), ratio of std to mean breathing rate (BR std/mean), mean peak-to-peak amplitude of a breathing signal (Amp. Mean), standard deviation of peak-to-peak amplitude of the breathing signal (Amp. std), ratio of standard deviation to mean of peak-to-peak amplitude of the breathing signal (Amp. std/mean), mean absolute deviation of sequential differences of peak-to-peak amplitude of the breathing signal (Amp. MADSD), and root-mean-square of sequential differences of peak-to-peak amplitude of the breathing signal.

The time-frequency respiratory features first require transforming a detected respiratory signal in a predetermined time period to the frequency domain by using a short time Fourier transform (STFT). The plurality of features related to the time-frequency respiratory features include but are not limited to the power in the in the VLF band of the breathing signal between 0.01-0.04 Hz (VLF of resp.), power in the LF band of the breathing signal between 0.04-0.15 Hz (LF of resp.), power in the HF band of the breathing signal between 0.15-0.4 Hz (HF of resp.), ratio of the power in the HF to LF bands (HF/LF of resp.), peak power in the VLF band of the breathing signal (VLF max of resp.), peak power in the LF band of the breathing signal (LF max of resp.), peak power in the HF band of the breathing signal (HF max of resp.), frequency at which the peak power occurs in the VLF band (Freq. of VLF max), frequency at which the peak power occurs in the LF band (Freq. of LF max), frequency at which the peak power occurs in the HF band (Freq. of HF max), entropy of power spectral density (PSD) by treating it as a probability density function (PDF), kurtosis of the PSD by treating it as a PDF (Kurtosis of resp.), and ratio of the max power in the PSD to the average power in the PSD (Peak-Mean-Ratio of resp.).

The cross-spectral respiratory features first require that a cross-spectrum be calculated using a cross-spectrum between a breathing signal and a R-R interval signal where the coherence is defined as a cross-spectrum normalized by the autospectra of the breathing and the R-R interval signals. This is done to obtain cross-spectral information from the two signals (breathing signal and R-R interval signal). The plurality of features related to the cross-spectral respiratory features include but are not limited to the entropy of the cross-spectrum when it is treated as a PDF (Entropy of cross-spectrum), kurtosis the cross-spectrum when it is treated as a PDF (Kurtosis of cross-spectrum), ratio of the max power to the average power of the cross-spectrum (Peak-Mean-Ratio of cross-spectrum), entropy of the coherence when treated as a PDF (Entropy of coherence), kurtosis of the coherence when treated as a PDF (Kurtosis of coherence), and the ratio of the max coherence to the average coherence (Peak-Mean-Ratio of coherence).

The other features include but are not limited to the average skin temperature of a predetermined time period (Mean temperature), average rate of change of the skin temperature over a predetermined time period (Slope of temperature), mean angle phi ($\phi$) of the body that determines a sleeping position such as supine, left, right, prone ($\phi$ mean), signal magnitude area (SMA) of the accelerometer signals (SMA), and number of seconds since initial bed entry (Time since bed entry).

After feature extraction, the plurality of features can be scaled so that a subsequent machine learning classifier is able to deal with features of varying magnitudes. In one embodiment, the plurality of features are scaled by normalizing each feature within a training data set used by the machine learning classifier so that the minimum to maximum values lie within the range of 0 to 1. If another embodiment, the plurality of features are scaled by normalizing each feature within the training data set so that the mean of the feature is 0 and the standard deviation is 1.

After feature extraction, each epoch has a set of features associated with it (the feature vector X). The set of features and the feature vector X are used as an input to a machine learning classifier unit of the wireless sensor device. The machine learning classifier unit outputs a set of probabilities or "confidence" values that each epoch is associated with one of the 5 possible sleep stages. The machine learning classifier unit may be any classifier in which probabilistic outputs can be obtained or estimated, including but not limited to a support vector machine (SVM), a Naïve Bayes classifier (NBC), and a random forest classifier (RF).

In one embodiment, to train the machine learning classifier utilized by the wireless sensor device, a data set that includes PSG-derived sleep stages for each epoch that was previously determined is obtained. Therefore, each epoch has a PSG-derived value for the sleep stage and the machine learning classifier unit learns the best mapping of features to predict the sleep stage as accurately as possible. In another embodiment, data sets are extracted wirelessly from other users of similar wireless sensor devices and inputted into a centralized database that is then utilized to train the machine learning classifier.

In one embodiment, a support vector machine (SVM) machine learning classifier is utilized by the wireless sensor device to automatically classify each epoch of the plurality of epochs into one of the 5 stages of sleep. Given one epoch (and associated feature vector X), a set of SVMs output confidence values (d) for each possible sleep stage (Y={W, N1, N2, N3, REM}). The confidence values can be any real number and correspond to the distance of the point away from the decision boundaries. The more positive that the confidence value is correlates with more confidence in the classification of that sleep stage by the machine learning classifier.

The distance is converted to a probability by fitting a sigmoid function to each of the SVM classifiers. The conversion into a probability enables adjustment via temporal dynamics and estimates a posterior probability P(Y|X) where Y is the class (sleep stage), X is the feature vector, d is the confidence value, and A and B are fit sigmoid parameters (A is typically negative) per the equation $$P(Y\mid X) \approx \frac{1}{1+e^{A\cdot d+B}}.$$

Temporal dynamics adjustment can be utilized to smooth the outputted results from the machine learning classifier unit and the sleep stage classifications. If temporal dynamics adjustment is not utilized, the machining learning classifier classifies each epoch independently and does not consider previously occurring epochs. In this embodiment, the outputs of the SVM of the wireless sensor device are used as the final classification of the sleep stages by choosing the sleep stage with the largest posterior probability $P(Y=y_i|X)$ for each epoch.

In one embodiment, temporal dynamics adjustment is utilized by the wireless sensor device after the machine learning classifier initially classifies each epoch based upon posterior probabilities. Considering the temporal dynamics of sleep can improve the automated sleep staging. For example, it is rare to go straight from being awake to stage N3 or REM sleep and deeper sleep stages are more likely early in the night and REM is more likely later in the night. Therefore, the wireless sensor device continually considers temporal dynamics and learns about what previous epochs were classified as to help with the classification of the current epoch that is being analyzed. In another embodiment, an algorithm processing unit of a remote server utilizes an algorithm to continually consider temporal dynamics and learns about what previous epochs were classified as to help with the classification of the current epoch that is being analyzed.

The wireless sensor device or the algorithm processing unit of the remote server utilizes the algorithm to process and to adjust the outputs of the machine learning classifier based on temporal dynamics thereby filtering the sleep stage predictions/probabilities. In one embodiment, the algorithm is a Hidden Markov Model (HMM) that uses output probabilities to adjust prediction. HMM is a machine learning algorithm that functions on sequential, time-dependent data, and considers probabilities of transitioning between various states to take temporal dynamics into account.

The HMM assumes that there are a set number of "hidden" states $(y_1, y_2, \ldots, y_N)$ that cannot be observed directly and the states are the 5 stages of sleep (W, N1, N2, N3, REM). At each point in time (n), only a set of observed features $(X_n)$ is measured and the values of these variables depends on the current state. The HMM requires the calculation of the likelihood of a set of features given each of the possible states/classes which is given per the equation $P(X_n|Y_n)$ and requires the probability of each state, given the previous state which is given per the equation $P(Y_n=y_i|Y_{n-1}=y_j)$. The probably of each state given the previous state are transition probabilities and are represented by a transition probability matrix A where $A_{ij}=P(Y_n=y_n|Y_{n-1}=Y_j)$.

The HMM predicts the most likely sequence of states (sleep stages) given the likelihoods, $P(X_n|Y_n)$, prior probabilities, and transition probabilities. The machine learning classifier, or SVM, outputs posterior probabilities $P(Y_n|X_n)$ so these values are converted to likelihoods $P(X_n|Y_n)$ using Bayes Rule given a learned set of prior probabilities $P(Y)$ per the equation $$P(X_n|Y_n) \propto \frac{P(Y_n|X_n)}{P(Y)}.$$

In another embodiment, instead of assuming a time-invariant transition matrix, A, and prior probabilities, P(Y), a time-varying transition matrix A[n] and prior probability P(Y[n]) is used. This reflects the changing probabilities of different sleep stages as the night progresses as previously discussed (e.g. N3 is more common early in the night, REM is more common later in the night).

Figure 3:
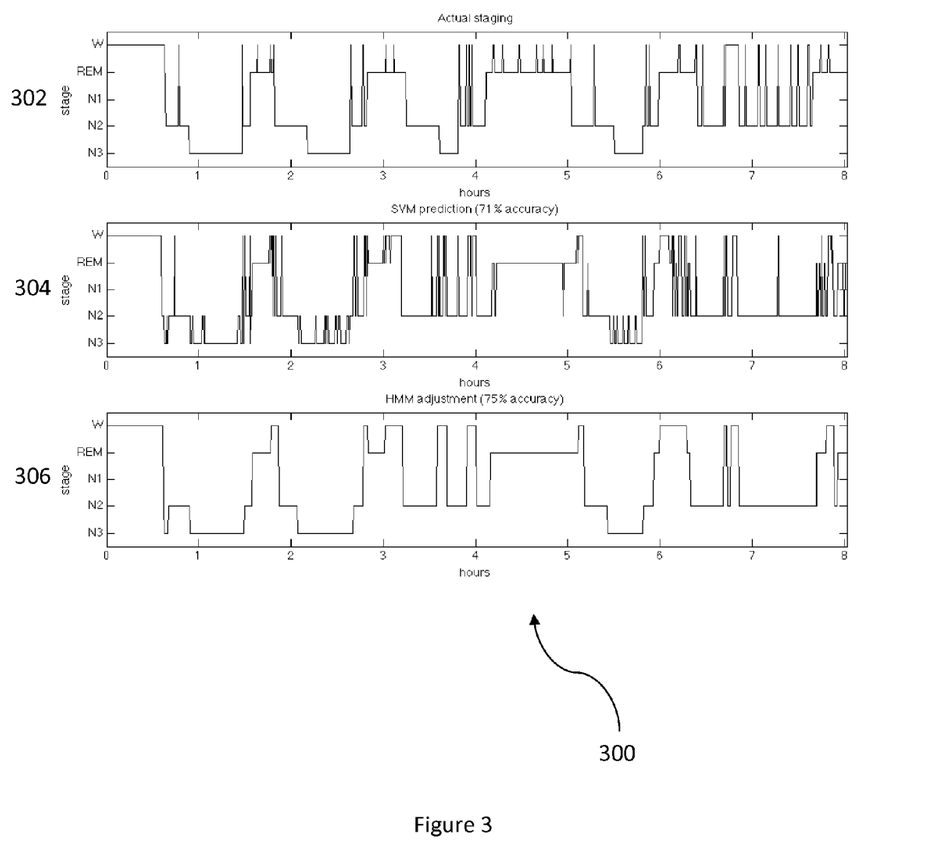
FIG. 3 illustrates a diagram comparing PSG study results to automated sleep staging results in accordance with an embodiment.

FIG. 3 illustrates a diagram 300 comparing PSG study results to automated sleep staging results in accordance with an embodiment. The diagram 300 includes a first graph 302 depicting a PSG study that results in control staging results. The diagram includes a second graph 304 depicting automated sleep staging in accordance with the method 200. The automated sleep staging classifies the sleep stages with 71% accuracy compared to the control staging results. The diagram includes a third graph 306 depicting automated sleep staging in accordance with the method 200 coupled with HMM temporal dynamics adjustment. The HMM temporal dynamics adjustment improves the accuracy to 75% compared to the control staging results.

Figure 4:
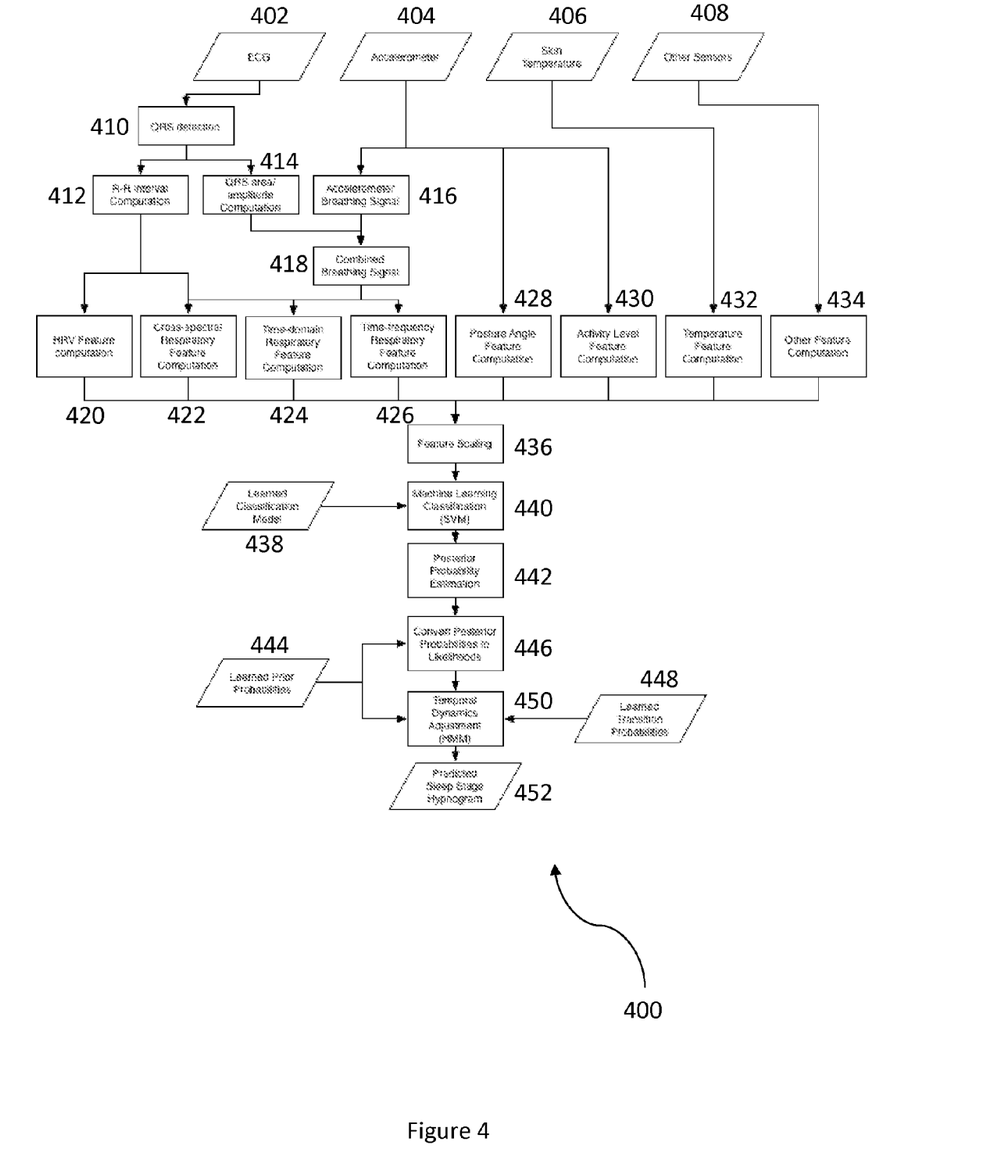
FIG. 4 illustrates another method for automated sleep staging by a wireless sensor device in accordance with an embodiment.

FIG. 4 illustrates another method 400 for automated sleep staging by a wireless sensor device in accordance with an embodiment. In the method 400, the wireless sensor device detects various physiological signals including ECG signals by an ECG sensor via step 402, accelerometer signals by an accelerometer sensor via step 404, skin temperature signals by a temperature sensor via step 406, and other signals (e.g. EEG) by other sensors via step 408. After detecting the ECG signals, the wireless sensor device utilizes the detected ECG signals to detect the QRS via step 410 and utilizes the detected QRS to calculate R-R intervals via step 412 and QRS area/amplitude via step 414. After detecting the accelerometer signals, the wireless sensor device utilizes the detected accelerometer signals to detect an accelerometer breathing signal based on the movement of the chest wall during respiration via step 416 and the QRS area/amplitude signal is combined with the accelerometer breathing signal using a least-means-squared (LMS) algorithm to obtain a combined breathing signal via step 418.

The wireless sensor device feeds the R-R intervals, QRS area/amplitudes, breathing signals, skin temperature signals, and other sensor signals into a feature extraction unit that calculates and extracts various features from these physiological signals. The calculated R-R intervals are used to calculate HRV features via step 420 and cross-spectral respiratory features via step 422. The calculated QRS area/amplitudes and the calculated breathing signals are used to calculate cross-spectral respiratory features via step 422, time-domain respiratory features via step 424, and time-frequency respiratory features via step 426. Other accelerometer signal data is utilized to calculate posture angle features via step 428 and activity level features via step 430. The skin temperature signals are used to calculate temperature features via step 432 and the other signals are used to calculate other features via step 434.

After extracting all of the features from the physiological signals via steps 420-434, the wireless sensor device scales the features via step 436. A machine learning classifier unit of the wireless sensor device performs machine learning classification via step 440 based upon learned classification models via step 438. The wireless sensor device utilizes the outputs of the machine learning classifier to estimate posterior probabilities via step 442 classifying each epoch into one of the 5 stages of sleep. The posterior probabilities are converted into likelihoods via step 446 based upon learned prior probabilities via step 444. The wireless sensor device performs temporal dynamics adjustment on the outputted likelihood results via step 450 based upon learned transition probabilities via step 448. After the temporal dynamics adjustment, a predicted sleep stage hypnogram is created by the wireless sensor device or the algorithm processing unit of the remote server via step 452 that displays the automated sleep staging process of the method 400.

The machine learning classifier of the wireless sensor device requires training data sets to learn relationships between features and outputs for the initial prediction of sleep stages and also for the potential subsequent adjustment based on temporal dynamics. In FIG. 4, the learned classification models, learned prior probabilities and learned transition probabilities require the inputting of initial training data sets into the machine learning classifier of the wireless sensor device.

In the case of SVM, or other machine learning classifiers, a training data set containing feature vectors and corresponding labels (e.g. sleep stages as identified by a sleep doctor during a PSG study) is used to train the algorithm and the machine learning classifier. The algorithm learns the mapping from feature vectors to sleep stages and produces a machine learning model. In the case of HMM, the prior probabilities of the sleep stages and the transition probabilities are trained from a training data set. In one embodiment, the training data set is used to train the prior probabilities of the sleep stages per the equation $P(Y=y_i)=$(number of epochs that are sleep stage i)/(total number of epochs). In one embodiment, the training data set is used to train the transition probabilities which are calculated using the sequence of true sleep stages from the training data set per the equation $A_{ij}=$(number of times transitioned from stage j to stage i)/(number of times in stage j). These equations utilize the training data to estimate the underlying probabilities of the parameters in the HMM.

As above described, a method and system in accordance with the present invention utilizes a wireless sensor device that detects and analyzes various physiological signals of a user to automatically and continuously classify the 5 stages of sleep. By integrating machine learning classifiers, the final classification of the sleep stages is automated and does not require external monitoring by a technician as is the case in a traditional PSG study. Additionally, temporal dynamics adjustment can be utilized to smooth out the outputted results and arrive at a predicted sleep stage hypnogram.

A method and system for automated sleep staging by a wireless sensor device have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A wireless sensor device for automated sleep staging, the wireless sensor device comprising:
a sensor to determine at least one physiological signal;
a processor coupled to the sensor; and
a memory device coupled to the processor, wherein the memory device includes an application that, when executed by the processor, causes the processor to:
extract at least one feature from each of a plurality of epochs of the at least one physiological signal;
scale the at least one feature for each epoch;
determine a feature vector for each epoch using the at least one scaled feature; and
classify each epoch into one of a plurality of sleep stages by inputting each feature vector into a machine learning classifier unit, wherein the at least one scaled feature enables the machine learning classifier unit to classify epochs with features of varying magnitudes.

2. The wireless sensor device of claim 1, wherein the application, when executed by the processor, further causes the processor to:
adjust the at least one outputted sleep stage based on temporal dynamics.

3. The wireless sensor device of claim 1, wherein the at least one physiological signal includes any of an electrocardiogram (ECG) signal, a microelectromechanical system (MEMS) accelerometer signal, a skin temperature signal, and an electroencephalography (EEG) signal.

4. The wireless sensor device of claim 1, wherein the predetermined time period is every four minutes over eight continuous hours and wherein the at least one sleep stage is any of W, N1, N2, N3, and REM sleep stages.

5. The wireless sensor device of claim 1, wherein the machine learning classifier unit is located on any of the processor of the wireless sensor device and a remote server, further wherein the machine learning classifier unit includes any of a support vector machine (SVM) unit, a Naïve Bayes classifer (NBC) unit, and an artificial neural network (ANN) unit.

6. The wireless sensor device of claim 1, wherein the processor includes both the machine learning classifier unit and an algorithm unit, further wherein the machine learning classifier unit is a support vector machine (SVM) unit.

7. The wireless sensor device of claim 6, wherein the application, when executed by the processor, further causes the processor to:
output a plurality of class probabilities via the support vector machine (SVM) unit; and input the plurality of outputted class probabilities into the algorithm unit that adjusts the plurality of outputted class probabilities based on temporal dynamics.

8. The wireless sensor device of claim 6, wherein the algorithm unit utilizes a Hidden Markov Model (HMM) algorithm that considers temporal dynamics of stage transitions to smooth the plurality of outputted class probabilities.

9. The wireless sensor device of claim 1, wherein the application, when executed by the processor, further causes the processor to:
    train the machine learning classifier unit using a data set of sleep stages derived from a polysomnography (PSG) study.

* * * * *